United States Patent
Azria et al.

(10) Patent No.: US 9,272,040 B2
(45) Date of Patent: *Mar. 1, 2016

(54) 5-CNAC AS ORAL DELIVERY AGENT FOR PARATHYROID HORMONE FRAGMENTS

(75) Inventors: Moise Azria, Basel (CH); Simon David Bateman, Randolph, NJ (US)

(73) Assignee: Novartis AG, Basel (CH)

( * ) Notice: Subject to any disclaimer, the term of this patent is extended or adjusted under 35 U.S.C. 154(b) by 959 days.

This patent is subject to a terminal disclaimer.

(21) Appl. No.: 13/327,114

(22) Filed: Dec. 15, 2011

(65) Prior Publication Data

US 2012/0088725 A1   Apr. 12, 2012

Related U.S. Application Data

(63) Continuation of application No. 12/495,966, filed on Jul. 1, 2009, which is a continuation of application No. 11/443,528, filed on May 30, 2006, now abandoned, which is a continuation of application No. 10/484,331, filed as application No. PCT/EP02/09181 on Aug. 16, 2002, now abandoned.

(60) Provisional application No. 60/313,048, filed on Aug. 17, 2001.

(51) Int. Cl.
*A61K 38/29* (2006.01)
*A61K 47/18* (2006.01)
*A61K 9/48* (2006.01)
*A61K 31/198* (2006.01)

(52) U.S. Cl.
CPC ............ *A61K 47/183* (2013.01); *A61K 9/4858* (2013.01); *A61K 31/198* (2013.01); *A61K 38/29* (2013.01)

(58) Field of Classification Search
CPC ...................................................... A61K 38/29
USPC ........................................................ 514/11.8
See application file for complete search history.

(56) References Cited

U.S. PATENT DOCUMENTS 5,773,647 A    6/1998   Leone-Bay et al.

FOREIGN PATENT DOCUMENTS

| WO | WO 94/07514 | 4/1994 |
| WO | WO 00/59863 | 10/2000 |
| WO | WO 02/098453 | 12/2002 |

OTHER PUBLICATIONS

Leone-Bay et al., "Oral Delivery of Biologically Active Parathyroid Hormone", Pharmaceutical Research, vol. 18, No. 7, pp. 964-970, (2001).
Leone-Bay et al., "Synthesis and Evaluation of Compounds That Facilitate the Gastrointestinal Absorption of Heparin", Journal of Medicinal Chemistry, vol. 41, No. 7, pp. 1163-1171, (1998).
Fox J. et al., "Plasma Levels of Parathyroid Hormone That Induce Anabolic Effects in Bone of Ovariectomized Rats Can Be Achieved by Stimulation of Endogenous Hormone Secretion", Bone, vol. 21, No. 2, pp. 163-169, (1997).
Forteo® Package Insert, Eli Lilly & Co., Revised, Feb. 27, 2008.

*Primary Examiner* — David Lukton
(74) *Attorney, Agent, or Firm* — Ann R. Pokalsky; Dilworth & Barrese, LLP

(57) ABSTRACT

Pharmaceutical compositions for the effective oral delivery of a parathyroid hormone, PTH, as well as methods for administration of the compositions are provided. Additionally, methods for stimulating new bone formation and treating and/or preventing osteoporosis are also provided.

5 Claims, No Drawings

5-CNAC AS ORAL DELIVERY AGENT FOR PARATHYROID HORMONE FRAGMENTS

This application is a continuation of application Ser. No. 12/495,966 filed Jul. 1, 2009 now abandoned, which is a continuation of application Ser. No. 11/443,528 filed on May 30, 2006, now abandoned, which is a continuation of application Ser. No. 10/484,331 filed on Jun. 3, 2004, now abandoned, which is a National Stage of International Application No. PCT/EP02/09181 filed on Aug. 16, 2002, which claims benefit of provisional Application No. 60/313,048 filed on Aug. 17, 2001, the entire disclosures of which are hereby incorporated by reference.

BACKGROUND OF THE INVENTION

1. Field of the Invention

The present invention relates to the oral delivery of parathyroid hormone (PTH). The mammalian parathyroid hormones, e.g. human (hPTH), bovine (bPTH) and porcine (pPTH), are single polypeptide chains of 84 amino acid residues having molecular weights of approximately 9500. Specifically, the present invention relates to PTH fragments incorporating at least the first 28 N-terminal amino acid residues (PTH (1-28)) up to and including the first 41 N-terminal amino acid residues (PTH (1-41)). More particularly, the invention is directed to pharmaceutical compositions for the oral delivery of PTH, said compositions comprising PTH (1-28) to (1-41) and N-(5-chlorosalicyloyl)-8-aminocaprylic acid (5-CNAC).

2. Description of the Related Art

PTH studies done in animals and humans with PTH, PTH-related peptides, and PTH analogues have demonstrated its usefulness in increasing bone formation and bone resorption and have prompted interest in its use for the treatment of osteoporosis and related bone disorders. However, the oral delivery of PTH in mammals has proven difficult due, at least in part, to the insufficient stability of PTH in the gastrointestinal tract as well as the inability of PTH to be readily transported through the intestinal walls into the blood stream.

U.S. Pat. No. 5,773,647 (the '647 patent) describes 193 carrier compounds useful for the delivery of active agents, including PTH. One of the carrier compounds expressly described therein is N-(5-chlorosalicyloyl)-8-aminocaprylic acid (5-CNAC) having the formula

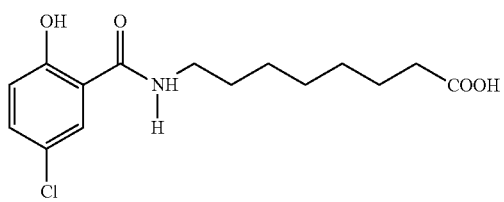 [SMILES: O=C(O)CCCCCCCNC(=O)c1cc(Cl)ccc1O]

Example 2 in Column 6 of the '647 patent describes the preparation of 11 different dosing compositions some intracolonic (IC) and some oral gavage (PO) each containing parathyroid hormone and a carrier, the carrier being different for each composition. An IC dosing composition was prepared using 5-CNAC as the carrier. Example 3 therein describes in vivo tests carried out dosing male Sprague-Dawley rats with the dosing solutions prepared in Example 2. Blood samples were collected and the serum PTH concentration was quantified for each rat.

Surprisingly, it has now been found that 5-CNAC in combination with specific PTH fragments, i.e. PTH fragments incorporating at least the first 28 N-terminal amino acid residues (PTH (1-28)) up to and including the first 41 N-terminal amino acid residues (PTH (1-41)) when orally administered gives unexpectedly high PTH serum levels relative to other PTHs and other carriers and provide a sharp $C_{max}$ allowing for a bone formation effect.

SUMMARY OF THE INVENTION

Accordingly, the present invention is directed to pharmaceutical compositions suitable for oral delivery of PTH fragments and to methods of administering such compositions.

Specifically, the instant invention is directed to a pharmaceutical composition for oral delivery comprising a therapeutically effective amount of a PTH fragment and 5-CNAC, said PTH fragment selected from PTH (1-28) to PTH (1-41). Preferably, the PTH is human parathyroid hormone, hPTH.

In another embodiment, the invention is directed to a method for orally administering an effective dose of PTH comprising orally administering to a patient in need of PTH a pharmaceutical composition comprising a therapeutically effective amount of a PTH fragment and 5-CNAC, said PTH fragment selected from PTH (1-28) to PTH (1-41).

The invention is also directed to a method of stimulating new bone formation comprising orally administering to a patient in need of new bone formation a pharmaceutical composition comprising a therapeutically effective amount of a PTH fragment and 5-CNAC, said PTH fragment selected from PTH (1-28) to PTH (1-41).

In a further embodiment, the invention is directed to a method of treatment or prevention of osteoporosis comprising orally administering to a patient in need of said treatment or prevention a pharmaceutical composition comprising a therapeutically effective amount of a PTH fragment and 5-CNAC, said PTH fragment selected from PTH (1-28) to PTH (1-41).

In a still further embodiment, the invention is directed to the use of 5-CNAC for the preparation of a pharmaceutical composition suitable for the oral delivery of PTH fragments selected from PTH (1-28) to PTH (1-41).

Further features and advantages of the invention will become apparent from the following following detailed description of the invention.

DETAILED DESCRIPTION OF THE INVENTION

The PTH fragments can be of any parathyroid hormone, particularly mammalian parathyroid hormone, e.g. human (hPTH), bovine (bPTH), and porcine (pPTH) and particularly hPTH and will incorporate at least the first 28 N-terminal residues (PTH (1-28)) up to and including the first 41 N-terminal residues (PTH (1-41)) and include without limitation PTH (1-28), PTH (1-31), PTH (1-34), PTH (1-37), PTH (1-38) and PTH (1-41). Human parathyroid hormone (1-34) is particularly preferred. These parathyroid hormone fragments are commercially available or can be obtained recombinantly or by peptide synthesis.

For purposes of the instant invention, the 5-CNAC, i.e. N-(5-chlorosalicyloyl)-8-aminocaprylic acid, can be the free acid, analogs thereof, its monosodium and disodium salts, ethanol solvates of the sodium salts and the monohydrates of the sodium salts and any combinations thereof. The free acid, the disodium salt of 5-CNAC and the monohydrate thereof are particularly useful. N-(5-chlorosalicyloyl)-8-aminocaprylic acid is described in the aforementioned '647 patent, the contents of which are hereby incorporated by reference, and can be made by methods described therein. The sodium salts and alcohol solvates and hydrates thereof are described in WO 00/059863, along with methods for preparing them.

The disodium salt may be prepared from the ethanol solvate by evaporating or drying the ethanol solvate by methods known in the art to form the anhydrous disodium salt. Drying is generally carried out at a temperature of from about 80 to about 120° C., preferably from about 85 to about 90° C., and most preferably at about 85° C. The drying step is generally performed at a pressure of 26" Hg or greater. The anhydrous disodium salt generally contains less than about 5% by weight of ethanol and preferably less than about 2% by weight of ethanol, based on 100% total weight of anhydrous disodium salt.

The disodium salt of N-(5-chlorosalicyloyl)-8-aminocaprylic acid can also be prepared by making a slurry of N-(5-chlorosalicyloyl)-8-aminocaprylic acid in water and adding two molar equivalents of aqueous sodium hydroxide, sodium alkoxide or the like. Suitable sodium alkoxides include, but are not limited to, sodium methoxide, sodium ethoxide, and combinations thereof.

A still further method of preparing the disodium salt is by reacting N-(5-chlorosalicyloyl)-8-aminocaprylic acid with one molar equivalent of sodium hydroxide to form a monosodium salt and then adding an additional one molar equivalent of sodium hydroxide to yield the disodium salt.

The disodium salt can be isolated as a solid by concentrating the solution containing the disodium salt to a thick paste by vacuum distillation. This paste may be dried in a vacuum oven to obtain the disodium salt of N-(5-chlorosalicyloyl)-8-aminocaprylic acid as a solid. The solid can also be isolated by spray drying an aqueous solution of the disodium salt.

The ethanol solvates, as described in the aforementioned WO 00/059863, include, but are not limited to, a molecular or ionic complex of molecules or ions of ethanol solvent with molecules or ions of the disodium salt of N-(5-chlorosalicyloyl)-8-aminocaprylic acid. Typically, the ethanol solvate contains about one ethanol molecule or ion for every molecule of disodium salt of N-(5-chlorosalicyloyl)-8-aminocaprylic acid.

The ethanol solvate of the disodium salt of N-(5-chlorosalicyloyl)-8-aminocaprylic acid can be prepared by dissolving N-(5-chlorosalicyloyl)-8-aminocaprylic acid in ethanol. Typically, each gram of N-(5-chlorosalicyloyl)-8-aminocaprylic acid is dissolved in from about 1 to about 50 mL of ethanol and generally, from about 2 to about 10 mL of ethanol. The N-(5-chlorosalicyloyl)-8-aminocaprylic acid/ethanol solution is then reacted with a molar excess of a sodium containing salt, such as a monosodium containing salt, relative to N-(5-chlorosalicyloyl)-8-aminocaprylic acid, i.e. for every mole of N-(5-chlorosalicyloyl)-8-aminocaprylic acid there is more than one mole of sodium cations, yielding the ethanol solvate. Suitable monosodium salts include, but are not limited to, sodium hydroxide; sodium alkoxides, such as sodium methoxide and sodium ethoxide; and any combination of the foregoing. Preferably, at least about two molar equivalents of the monosodium containing salt are added to the ethanol solution, i.e. for every mole of N-(5-chlorosalicyloyl)-8-aminocaprylic acid there is at least about two moles of sodium cations. Generally, the reaction is performed at or below the reflux temperature of the mixture, such as at ambient temperature. The ethanol solvate is then recovered by methods known in the art, such as, concentration of the resulting slurry at atmospheric distillation, cooling the concentrated slurry and filtering the solid. The recovered solid can then be vacuum dried to obtain the ethanol solvate.

The hydrates of the disodium salts of the N-(5-chlorosalicyloyl)-8-aminocaprylic acid may be prepared by drying the ethanol solvate to form an anhydrous disodium salt, as described above, and hydrating the anhydrous disodium salt. Preferably, the monohydrate of the disodium salt is formed. Since the anhydrous disodium salt is very hydroscopic, the hydrate forms upon exposure to atmospheric moisture. Generally, the hydrating step is performed at from about ambient temperature to about 50° C., preferably ambient temperature to about 30° C. and in an environment having at least 50% relative humidity. Alternatively, the anhydrous disodium salt may be hydrated with steam.

The amount of PTH fragment to be administered is generally an amount effective to stimulate new bone formation i.e. a therapeutically effective amount. This amount will necessarily vary with the age, size, sex and condition of the subject to be treated, the nature and severity of the disorder to be treated and the like. However, the amount can be less than that amount when a plurality of the compositions are to be administered, i.e., the total effective amount can be administered in cumulative dosage units. The amount of PTH can also be more than the effective amount when the composition provides sustained release of the pharmacologically active agent. The total amount of PTH to be used can be determined by methods known to those skilled in the art. However, in general, satisfactory results will be obtained systemically at daily dosages of from about 0.001 µg/kg to about 10 mg/kg animal body weight, preferably 1 µg/kg to about 6 µg/kg body weight.

The pharmaceutical compositions of the present invention typically contain a delivery effective amount of 5-CNAC, i.e. an amount sufficient to deliver the PTH for the desired effect. Generally, the 5-CNAC is present in an amount of 2.5% to 99.4% by weight, more preferably 25% to 50% by weight of the total composition.

Oral administration of the pharmaceutical compositions according to the invention can be accomplished regularly, e.g. once or more on a daily or weekly basis; intermittently, e.g. irregularly during a day or week; or cyclically, e.g. regularly for a period of days or weeks followed by a period without administration.

The dosage form of the pharmaceutical compositions of the instant invention can be any known form, e.g. liquid or solid dosage forms.

The liquid dosage forms include solution emulsions, suspensions, syrups and elixirs. In addition to the PTH and 5-CNAC, the liquid formulations may also include inert excipients commonly used in the art such as, solubilizing agents e.g. ethanol; oils such as cottonseed, castor and sesame oils; wetting agents; emulsifying agents; suspending agents; sweeteners; flavorings; and solvents such as water.

The solid dosage forms include capsules, soft-gel capsules, tablets, caplets, powders, granules or other solid oral dosage forms, all of which can be prepared by methods well known in the art.

The pharmaceutical compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102 supplied by FMC corporation, or any combination thereof. Other additives may include phosphate buffer salts, citric acid, glycols, and other dispersing agents.

The composition may also include one or more enzyme inhibitors, such as actinonin or epiactinonin and derivatives thereof; aprotinin, Trasylol and Bowman-Birk inhibitor.

Further, a transport inhibitor, i.e. a p-glycoprotein such as Ketoprofin, may be present in the compositions of the present invention.

The solid pharmaceutical compositions of the instant invention can be prepared by conventional methods e.g. by blending a mixture of the PTH fragment, the 5-CNAC, and any other ingredients, kneading, and filling into capsules or, instead of filling into capsules, molding followed by further tableting or compression-molding to give tablets. In addition, a solid dispersion may be formed by known methods followed by further processing to form a tablet or capsule.

Preferably, the ingredients in the pharmaceutical compositions of the instant invention are homogeneously or uniformly mixed throughout the solid dosage form.

Parathyroid hormones are indicated for preventing or treating all bone conditions which are associated with increased calcium depletion or resorption or in which stimulation of bone formation and calcium fixation in the bone is desirable, e.g. osteoporosis of various genesis (e.g. juvenile, menopausal, post-menopausal, post-traumatic, caused by old age or by corticoid-steroid therapy or inactivity), fractures, osteopathy, including acute and chronic states associated with skeletal demineralization, osteo-malacia, periodontal bone loss or bone loss due to arthritis or osteoarthritis or cancer (e.g. bone metastis) or for treating hypoparathyroidism.

Parathyroid hormones are particularly indicated for preventing or treating osteoporosis of various genesis.

According to a further embodiment of the invention, the PTH may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial®), vitamin D or an analogue thereof or an activator of PTH release, or bisphosphonates, e.g. clodronic acid, etidronic acid, pamidronic acid, aledronic acid, ibandronic acid, zoledronic acid, risedronic acid or tiludronic acid and salts and hydrates thereof.

When the PTH is administered in conjunction with, e.g. as an adjuvant to bone resorption inhibition therapy, dosages for the co-administered inhibitor will of course vary depending on the type of inhibitor drug employed, e.g. whether it is a steroid or a calcitonin, on the condition to be treated, whether it is a curative or preventive therapy, on the regimen and so forth.

The oral administration of the present invention may be to any animal in need thereof, including, but not limited to, mammals, such as rodents, cows, pigs, dogs, cats, and primates, particularly humans.

The following examples serve to further illustrate the invention.

Example 1

The following capsules are prepared as follows:
Capsules prepared from 800 μg hPTH* (Capsule 1A)
Capsules prepared from 400 mg 5-CNAC**/800 μg hPTH* (Capsule 1B)
*The PTH fragment is human parathyroid hormone, fragment 1-34 commercially available from Sigma. **The 5-CNAC is the disodium salt of N-(5-chlorosalicyloyl)-8-aminocaprylic acid.

The hPTH only capsules are prepared by weighing out 400 μg of the hPTH and placing it directly into each capsule. The hPTH/5-CNAC capsules are prepared as dry blends by weighing out the individual components blending them together to make a homogeneous mix and then hand filling 400 mg of the mix into each capsule.

Example 2

Primate Administration

The capsules prepared in Example 1 are administered to Rhesus monkeys as follows: four monkeys in a group are each dosed with one capsule prepared as in Example 1 as follows:

The Rhesus monkeys fast overnight prior to dosing and are restrained in chairs fully conscious, for the duration of the study period. The capsules are orally administered via a gavage tube followed by 10 ml of water.

Blood samples are collected at 0, 0.25, 0.5, 0.75, 1, 1.5, 2, 3, 4, 5, and 6 hours after administration. Plasma hPTH levels are determined by radioimmunoassay. The primate plasma PTH results from each group of monkeys are averaged and the maximum mean plasma calculated. The results for the PTH only group are reported in Table 1 and the results for the hPTH/5-CNAC group are reported in Table 2.

TABLE 1 hPTH ONLY
hPTH PLASMA CONCENTRATIONS (pg/mL) AFTER
ORAL ADMINISTRATION TO THE RHESUS MONKEY
Dose: 1 Capsule 1D

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| R927 | 0 | 0 | 0 | 0 | 0 | 0 | 0 | 0 | 0 | 0 | 0 |
| S982 | 0 | 0 | 0 | 0 | 0 | 0 | 0 | 0 | 0 | 0 | 0 |
| Mean | 0 | 0 | 0 | 0 | 0 | 0 | 0 | 0 | 0 | 0 | 0 |
| SD | 0 | 0 | 0 | 0 | 0 | 0 | 0 | 0 | 0 | 0 | 0 |
| SEM | 0 | 0 | 0 | 0 | 0 | 0 | 0 | 0 | 0 | 0 | 0 |

LLOQ = 25 pg/mL, concentrations below LLOQ were set to zero.

TABLE 2 hPTH/5-CNAC
hPTH PLASMA CONCENTRATIONS (pg/mL) AFTER
ORAL ADMINISTRATION TO THE RHESUS MONKEY
Dose: 1 Capsule 1B

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| R944 | 0 | 83 | 191 | 300 | 360 | 262 | 154 | 35 | 0 | 0 | 0 |
| S963 | 0 | 127 | 332 | 663 | 1258 | 150 | 34 | 0 | 0 | 0 | 0 |
| Mean | 0 | 105 | 262 | 482 | 809 | 206 | 94 | 17 | 0 | 0 | 0 |
| SD | 0 | 31 | 100 | 257 | 635 | 79 | 85 | 25 | 0 | 0 | 0 |
| SEM | 0 | 22 | 71 | 182 | 449 | 56 | 60 | 17 | 0 | 0 | 0 |

As can be seen from the data in Tables 1 and 2, the 5-CNAC significantly facilitates the oral delivery of the hPTH fragment. In addition, the data in Table 2 indicate a sharp $C_{max}$ in the PTH plasma profile allowing for a bone formation effect.

The foregoing embodiments and examples are given merely to illustrate the instant invention and are not intended to be limiting. Numerous other embodiments and variations are within the scope of the invention and readily accessible to those skilled in the art.

We claim:

1. A method for orally administering a dose of PTH (1-34) comprising orally administering to a patient in need thereof, a pharmaceutical composition in solid dosage form that comprises recombinant PTH (1-34) and 5-CNAC disodium salt, wherein said dose is effective to stimulate new bone formation.

2. A method of stimulating new bone formation comprising orally administering to a patient in need of new bone formation a pharmaceutical composition in solid dosage form comprising a therapeutically effective amount of recombinant PTH (1-34) and 5-CNAC disodium salt.

3. A method of treating osteoporosis comprising orally administering to a patient in need of said treatment a pharmaceutical composition in solid dosage form comprising a therapeutically effective amount of recombinant PTH (1-34) and 5-CNAC disodium salt.

4. The method of claim 2 wherein the solid dosage form is selected from capsules, soft-gel capsules, tablets, caplets, powders and granules.

5. The method of claim 3 wherein the solid dosage form is selected from capsules, soft-gel capsules, tablets, caplets, powders and granules.

* * * * *